US00PP09939P

United States Patent [19]

Friday

[11] Patent Number: Plant 9,939

[45] Date of Patent: Jul. 1, 1997

[54] PEACH TREE 'P.F. 27A'

[75] Inventor: Paul Jan Friday, Coloma, Mich.

[73] Assignee: Paul J. Friday, Coloma, Mich.

[21] Appl. No.: 572,874

[22] Filed: Dec. 18, 1995

[51] Int. Cl.[6] ..... A01H 5/00

[52] U.S. Cl. ..... Plt./43.2

[58] Field of Search ..... Plt./43.2

*Primary Examiner*—James R. Feyrer

*Attorney, Agent, or Firm*—Fred P. Kostka

[57] ABSTRACT

A new and distinct variety of peach, *Prunus persica* having the following unique combination of desirable features:

1. The new and distinct variety of peach tree is of moderate upright growth and a regular and productive bearer of peaches.
2. Producing a very firm fruit having a resilient flesh texture.
3. Blossoms are non-showy when in full bloom.
4. A substantially spherical fruit with an attractive red skin coloring over a majority of the surface.
5. Late maturing fruit of good taste.
6. A late maturing fruit of good storage and shelf life.

1 Drawing Sheet

ORIGIN OF VARIETY

The new peach tree (hereinafter referred to as the P.F. 27A peach tree) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, P.F. 27A, was a selection from one such a seedling population, and was based on the numerous superior genetic attributes of this tree which are described in the botanical descriptions to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of semi-dwarf, moderate upright growth and a regular and productive bearer of peaches. A distinct characteristic of the P.F. 27A peach tree is its medium vigor having very stubby new growth with short internodes. The buds are generally 1 inch apart on the new growth. The blossoms bloom in mid-season and are characterized by being contracted or partially spread in a ¾-inch diameter during full bloom. At the same time the petals of the blossoms are of lesser length than the length of petals of the normal showy blossom as exemplified by the Loring peach blossom.

The blossoms of the present peach tree at full bloom may be characterized as being non-showy. More specifically, the blossoms of the present peach tree have radially projecting and angularly spaced five blossom petals to form a blossom having a diameter of about ¾" measured across the blossoms.

The flesh of the fruit of the present peach tree is firm and is yellow.

The skin is smooth having moderate to little down and is of dark red color over about sixty percent to eighty percent (60% to 80%) of its surface at maturity. The red color overlays yellow. Where the red merges with the yellow, the yellow is mottled with the red to a clear light yellow. At maturity the peach is spherical having an average diameter of about 2¾".

The fruit has a firm flesh and may be described as resilient to the extent that the flesh is yieldable and restorable to its original state when subjected to impact forces which may cause bruising and soft blemishes which lead to rejection by the buyer in the fresh market in peaches of the commercial varieties. The firmness of the fruit facilitates handling and packaging of the peaches without damaging the same for shipment. This results in less spoilage and also increases the shelf life.

The fruit matures in the latter part of the peach growing season of southwestern Michigan. The fruit as mentioned heretofore is of red color over about sixty percent to eighty percent (60% to 80%) of its surface and has a very attractive appearance.

BRIEF DESCRIPTION OF THE PHOTOGRAPHS

In the accompanying photographic illustrations, the top photograph shows a stem of the tree taken at ripeness of fruit and harvest stage.

This photograph shows three whole specimens of fruit at different orientations while still attached to the stem, as well as one specimen of the fruit bisected at a ninety-degree angle to the plane of the suture, with the stone retained in the half at the top. The color of bearing wood, top and bottom leaf surfaces, leaf midribs, fruit skin color and patterns of coloration, fruit flesh color and color of flesh adjacent to the pit cavity are illustrated.

The bottom photograph depicts a typical stem of the tree at a stage near full bloom, with newly emerging leaves. The branching shown is typical and reflective of branch density on bearing portions of the tree. Flower density and character are depicted at anthesis.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:

*Height.*—Medium 12'.
*Width.*—Unpruned 12'.
*Size.*—Medium.
*Vigor.*—Medium vigor terminal growth of 12" to 18" per year.
*Density.*—Medium.
*Form.*—Upright to spreading; as wide as tall. Scaffold branches are strong with little or no bark encroachment in crotches. Trees are easily maintained to have a rounded figure if a central leader is retained, but are adaptable to other training systems by pruning if desired.
*Production.*—Very productive, approximately ⅔ of the fruit annually must be thinned off to obtain size described.
*Bearer.*—Very consistent.
*Disease resistance to bacterial leaf and fruit spot.*—Very good.

Trunk:

*Size.*—Medium.
*Surface.*—Medium shaggy caused by excess of small lenticels ¼" long.

Branches:

*Size.*—Medium.
*Surface.*—Somewhat rough caused by many very small lenticels.
*Lenticels.*—Above average number of small size, light in color.
*Color.*—Grayish brown.

Leaves:

*Size.*—Medium. Average length — 5" to 6". Average width — 1⅛".
*Form.*—Lanceolate — pointed.
*Thickness.*—Medium.
*Texture.*—Medium.
*Margin.*—Serrate.
*Petiole.*—Medium length — medium thickness.
*Gland.*—Normally 1 to 2 on both sides located on leaf and upper portion of petiole.
*Color.*—Upper surface: green (350c). Bottom: dull green (349c).

Flower buds:

*Size.*—Medium.
*Length.*—Medium.

Flowers:

*Blooming period.*—May 1, 1995 to May 6, 1995.
*Size.*—Medium — about ¾" diameter.
*Pollen.*—Present, self-fertilizing.
*Color.*—Dark pink.

Fruit:

*Maturity when described.*—Firm ripe.
*Date of first picking.*—Sep. 16, 1995. Fruit matures very evenly and can be harvested in two to three pickings.
*Harvest date.*—Determined by color, late in season.
*Date of last picking.*—Sep. 21, 1995.
*Size.*—Large sphere. Average diameter — 2¾".
*Form.*—Spherical.
*Suture.*—Slight indentations on both sides of pistil point.

Skin:

*Thickness.*—Medium.
*Texture.*—Tough — tenacious to skin.
*Tendency to crack.*—None.
*Down.*—Moderate to little.
*Color.*—Fruit is attractively 60%–80% blushed red, near (1797u). Where blush suffuses to a clear light yellow (1205u) ground color, there may be a mottling of varied intensity and distinctness.

Flesh:

*Texture.*—Firm — non-melting, absence of fiber.
*Ripens.*—Relatively even.
*Flavor.*—Excellent; sweet and good balance of sugar to acidity.
*Aroma.*—Pleasant.
*Color.*—Yellow (127u) with a slight amount of red when fully ripe. Pit cavity — red (1797u).

Stone:

*Type.*—Freestone.
*Size.*—Average length — 1½". Average width — ⅞". Average thickness — ¾".
*Form.*—Ovid.
*Base.*—Straight.
*Apex.*—Pointed.
*Sides.*—Nearly equal.
*Surface.*—Irregularly furrowed.
*Color.*—Brown to reddish brown (201u).
*Tendency to crack.*—None.

Use: Desert.
Shipping quality: Excellent.
Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing of Coloma, Mich.

What is claimed is:

1. A new and distinct variety of peach tree substantially as illustrated and described as a medium size tree with a distinct short stubby growth pattern, a consistent bearer of highly colored, large fruit for the very late peach growing season, said fruit at maturity being of spherical shape with firm flesh and red skin color covering 60% to 80% of the fruit, said maturity occurring about the same date as the Fayette peach.

* * * * *

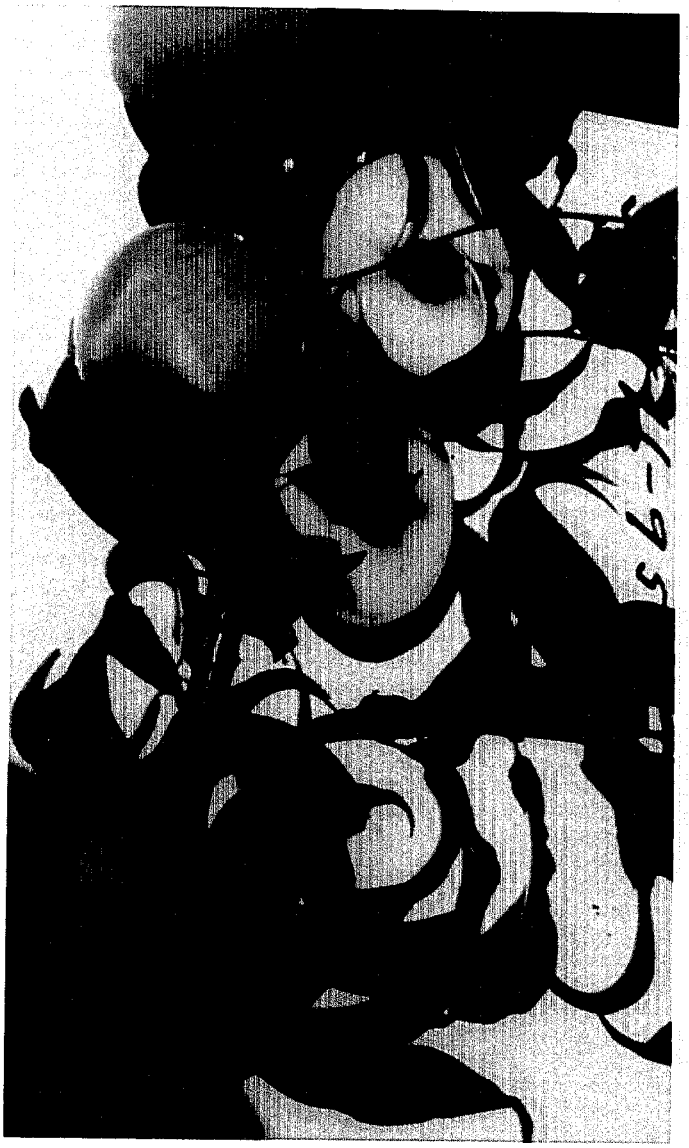
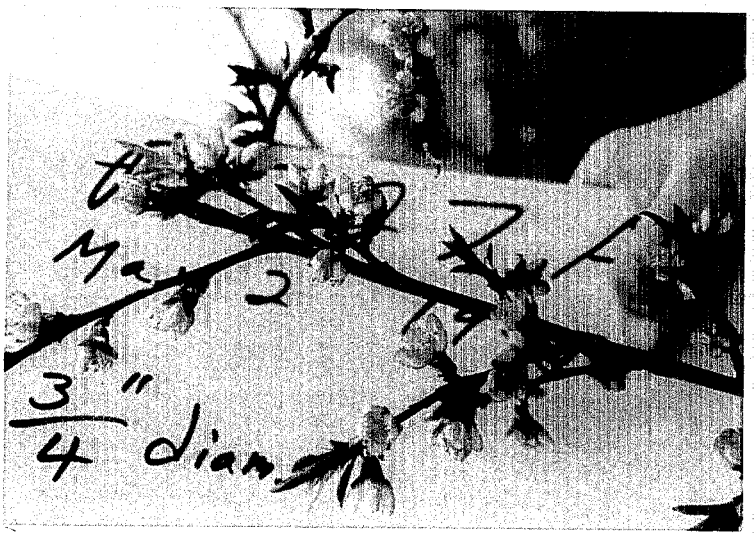
3/4" diam